United States Patent [19]

Meyer

[11] Patent Number: 4,816,590
[45] Date of Patent: Mar. 28, 1989

[54] PYRAZOLINE COMPOUNDS AND METHOD OF WHITENING

[75] Inventor: Hans R. Meyer, Binningen, Switzerland

[73] Assignee: Ciba-Geigy Corporation, Ardsley, N.Y.

[21] Appl. No.: 935,911

[22] Filed: Nov. 28, 1986

[30] Foreign Application Priority Data

Dec. 4, 1985 [CH] Switzerland .......................... 5163/85
Apr. 30, 1986 [CH] Switzerland .......................... 1770/86

[51] Int. Cl.$^4$ ..................... C07D 231/06; D06L 3/06; D06L 3/12
[52] U.S. Cl. ........................................ 548/379; 8/109; 252/301.27
[58] Field of Search ................... 548/379; 252/301.27; 8/109

[56] References Cited

U.S. PATENT DOCUMENTS

| 3,925,367 | 12/1975 | Boehmke et al. | 548/379 |
| 4,183,853 | 1/1980 | Schroeder | 548/379 |
| 4,263,431 | 4/1981 | Weber et al. | 548/379 |

FOREIGN PATENT DOCUMENTS

| 0073996 | 3/1983 | European Pat. Off. | 548/379 |
| 2700996 | 7/1978 | Fed. Rep. of Germany | 548/379 |
| 2755023 | 6/1979 | Fed. Rep. of Germany | 548/379 |
| 1431233 | 1/1966 | France | 548/379 |

OTHER PUBLICATIONS

Morrison et al., Organic Chemistry, 4th Ed., Alyn and Bacon, Boston (1983), pp. 919, 920.

Primary Examiner—Robert W. Ramsuer
Attorney, Agent, or Firm—Edward McC. Roberts

[57] ABSTRACT

The invention relates to pyrazoline compounds of formula

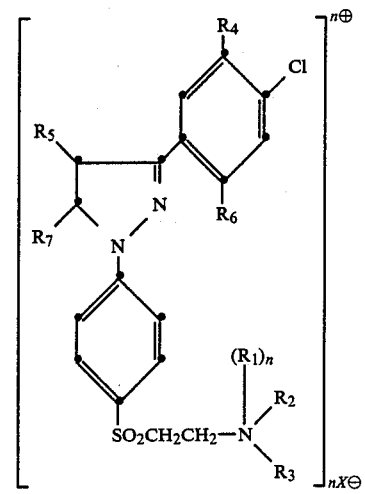

wherein $R_1$ is hydrogen or methyl, $R_2$ and $R_3$ are each independently of the other methyl, ethyl or hydroxyethyl, $R_4$ is hydrogen or chlorine, $R_5$ and $R_6$ are each independently of the other hydrogen or methyl, $R_7$ is hydrogen, methyl or phenyl, n is 0 or 1, with the proviso that, if n is 0 and $R_4$ to $R_7$ are hydrogen, $R_2$ is methyl and $R_3$ is hydroxyethyl, and $X^\ominus$ is a $C_1$-$C_3$alkanoate, $C_1$-$C_4$alkanephosphonate, $C_1$-$C_4$alkanesulfonate, phosphite, sulfamate or glycolate anion and, if $R_1$ is methyl, $X^\ominus$ is also a methosulfate, chloride or bromide ion, to the preparation of said compounds, to the use thereof as fluorescent whitening agents, and to novel hydrazine intermediates of formula

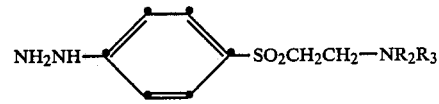

wherein $R_2$ and $R_3$ are methyl, ethyl or hydroxyethyl, and the acetone hydrazones and salts thereof.

3 Claims, No Drawings

PYRAZOLINE COMPOUNDS AND METHOD OF WHITENING

The present invention relates to novel pyrazoline compounds of formula

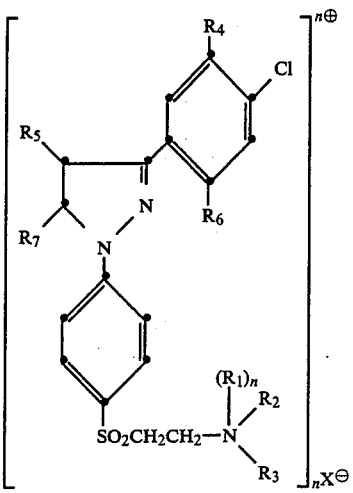

(1)

wherein $R_1$ is hydrogen or methyl, $R_2$ and $R_3$ are each independently of the other methyl, ethyl or hydroxyethyl, $R_4$ is hydrogen or chlorine, $R_5$ and $R_6$ are each independently of the other hydrogen or methyl, $R_7$ is hydrogen, methyl or phenyl, n is 0 or 1, with the proviso that, if n is 0 and $R_4$ to $R_7$ are hydrogen, $R_2$ is methyl and $R_3$ is hydroxyethyl, and $X^\ominus$ is a $C_1$-$C_3$alkanoate, $C_1$-$C_4$alkanephosphonate, $C_1$-$C_4$alkanesulfonate, phosphite, sulfamate or glycolate anion and, if $R_1$ is methyl, $X^\ominus$ is also a methosulfate, chloride or bromide ion.

The pyrazoline bases from which the novel salts are derived, with the exception of compounds of formula (5), are known from CH-A No. 455 802 and GB-A No. 1 204 953.

The invention preferably relates to compounds of formula

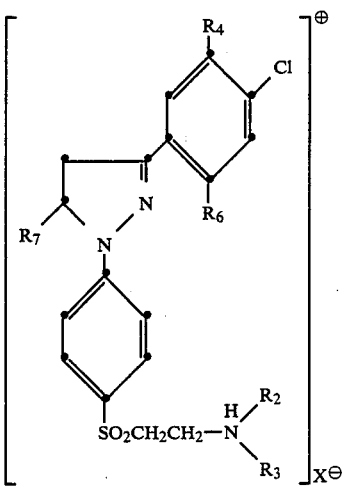

(2)

wherein $R_2$ to $R_4$, $R_6$ and $R_7$ are as defined for formula (1), and $X^\ominus$, on account of its particularly good properties for imparting water-solubility and resistance to heat and low temperatures, is a $C_1$-$C_3$alkanoate, $C_1$-$C_4$alkanephosphonate, $C_1$-$C_4$alkanesulfonate, phosphite, sulfamate or glycolate anion.

Particularly preferred pyrazoline compounds are those of formula

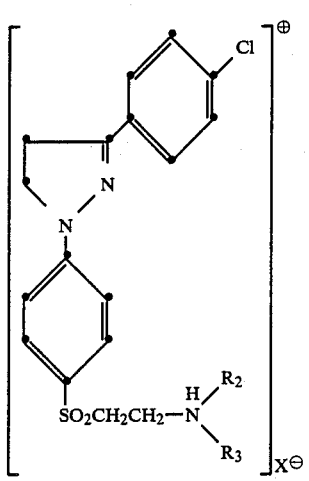

(3)

wherein $R_2$ and $R_3$ are each independently of the other methyl, ethyl or hydroxyethyl, and $X^\ominus$ is a $C_1$-$C_3$alkanoate, $C_1$-$C_4$alkanephosphonate, $C_1$-$C_4$alkanesulfonate, phosphite or sulfamate anion.

Further interesting quaternary compounds are those of formula

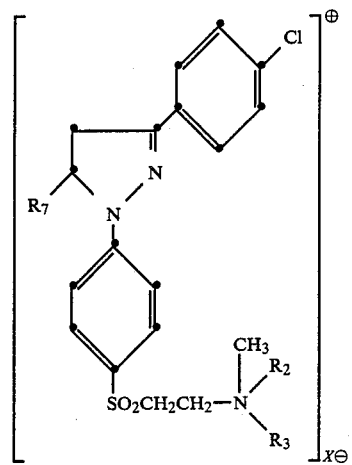

(4)

wherein $R_2$ and $R_3$ are each independently of the other methyl, ethyl or hydroxyethyl, $R_7$ is hydrogen or phenyl, and $X^\ominus$ is as defined in claim 1.

The pyrazoline bases (n=0) conform to the formula

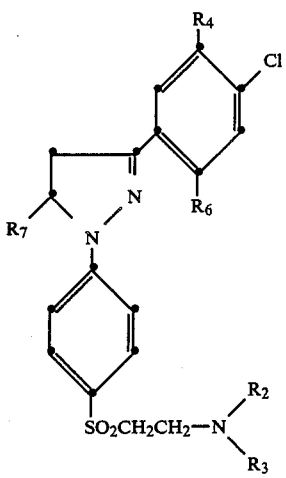

wherein $R_2$ to $R_4$, $R_6$ and $R_7$ are as defined for formula (1), with the proviso that, if $R_4$, $R_6$ and $R_7$ are hydrogen, $R_2$ is methyl and $R_3$ is hydroxyethyl.

Pyrazoline salts of formula (3), wherein $R_2$ and $R_3$ are both methyl and $X^\ominus$ is a formate, acetae, propionate, methanephosphonate, methanesulfonate, phosphate or sulfamate anion, have particularly advantageous properties. Particularly preferred pyrazoline salts of formula (3) are those containing a methanephosphonate, methanesulfonate, phosphite or sulfamate anion, with those containing a phosphite or sulfamate anion being most preferred.

Of particular commercial importance are aqueous solutions of one or more pyrazoline salts of formula (3), preferably aqueous solutions of one or more of the above pyrazoline salts with $C_1$-$C_3$alkanecarboxylic acids, especially of the preferred pyrazoline salts with acetic acid.

The pyrazoline compounds of formula I can be prepared by reacting pyrazolines of formula

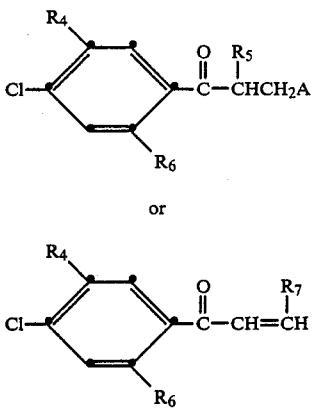

with dialkylamines of formula $HNR_2R_3$ and quaternising the reaction products with dimethyl sulfate, methyl chloride or methyl bromide, or protonising them with an acid of formula HX, in which formulae $R_2$ to $R_7$ and X are as defined for formula (1).

Another preferred process for the preparation of pyrazoline compounds of formula (1) comprises reacting ketones of formula

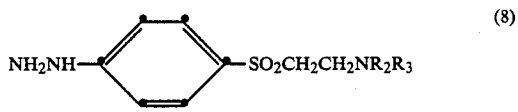

or

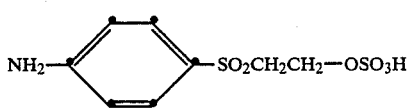

wherein A is halogen, a dialkylamino group containing 1 to 4 carbon atoms in the alkyl moieties, or a morpholino, pyrrolidino or piperidino radical, with hydrazines of formula

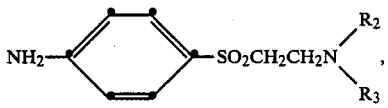

or the acetone hydrazones thereof, and, in a further optional step, subsequently quaternising or protonising the reaction products as described above.

Quaternisation or protonisation is effected in known manner, e.g. by reaction with dimethyl sulfate, methyl chloride or methyl bromide or by addition of the desired acid.

The hydrazines of formula (8), wherein $R_2$ and $R_3$ are each independently of the other methyl, ethyl or hydroxyethyl, and the salts and acetone hydrazones thereof, are novel and therefore constitute a further object of the invention. The hydrazines of formula (8) are obtained by treating the aniline of formula $$NH_2\text{—}\underset{}{\bigcirc}\text{—}SO_2CH_2CH_2\text{—}OSO_3H$$

with sodium hydroxide to give p-vinylsulfonyl aniline, and then reacting this compound with $HNR_2R_3$ to a compound of formula $$NH_2\text{—}\underset{}{\bigcirc}\text{—}SO_2CH_2CH_2N\genfrac{}{}{0pt}{}{R_2}{R_3},$$

which is then diazotised, reduced and saponified.

The acetone hydrazones are obtained by addition of acetone to the acid reaction mixture obtained in the synthesis of the hydrazines of formula (8), and subsequent addition of alkali until the reaction mixture is slightly alkaline.

The pyrazoline compounds of this invention, or mixtures thereof, are particularly suitable for whitening acrylic fibres by the exhaust process. By mixtures of compounds of formula (1) are meant those in which the substituents $R_1$ to $R_6$ are different and the anion $X^\ominus$ is the same, as well as those mixtures in which only the anion $X^\ominus$ is different in the compounds. The pyrazoline derivatives produce excellent white effects on acrylic as well as modified acrylic fibres (Courtelle fibres). They are also very effective on cellulose acetate, cellulose triacetate and polyamide fibres. They are particularly suitable for addition to polyacrylonitrile in the gel state, i.e. for incorporation in spinning solutions for fibre manufacture by the wet spinning method, e.g. on the basis of thiocyanate-containing spinning and precipitation baths. The whitened acrylic fibres have good fastness properties, in particular good wet lightfastness when bleaching with hydrogen peroxide in the presence of detergents and sodium perborate.

The bases of formula (1) (n=0) and formula (5) are used as intermediates for the preparation of the corresponding salts (n=1). In the quaternised compounds of formulae (1) ($R_1$=methyl) and (4), the methosulfate, chloride or bromide ions can be exchanged, e.g. by reverse osmosis, for the anions also cited. It is preferred, however, not to exchange the anions obtained in the quaternisation completely, but to prepare mixtures of anions by addition of the acid suitable for the protonation to the quaternised compounds.

The salts of formulae (1), wherein n=1 and $R_1$ is hydrogen, (2) and, in particular, (3), can be used in solid form or in solvents. They have particularly good water solubility at room temperature. The salts of other acids, e.g. the hydrochlorides, sulfates, phosphates, nitrates, oxalates and malonates, do not have these properties.

Stable solid formulations can be prepared from non-volatile or low-volatile acids such as phosphorus acid, sulfamic acid, methanesulfonic acid or methanephosphonic acid. This is done by stirring the pyrazoline base with the calculated amount of acid in a suitable organic solvent at 20°–80° C., whereupon the desired salt usually precipitates and can be filtered with suction. The reaction can also be carried out in water, in which case the solution is almost completely concentrated by evaporation and the product is precipitated with a suitable solvent in which the salt is sparingly soluble. Suitable solvents are in particular those that are miscible with water, such as methanol, ethanol, isopropanol, tert-butanol, acetonitrile, acetone, methyl ethyl ketone or dioxane.

Solid commercial formulations of cationic fluorescent whitening agents have a number of negative properties such as duet formation, poor flow properties, lump formation owing to agglommeration, unsuitability for automated addition to treatment baths, and an insufficient dissolving rate. These shortcomings can be avoided by using commercial formulations in the form of solutions. Such liquid formulations are also especially useful for whitening acrylic fibres in the gel state. Fairly concentrated solutions are employed in this method, depending on the dyeing unit and metering device. For this reason, particular importance attaches to the solubility of the fluorescent whitening agent and the stability of the solutions. The limits of the demands made of the solubility are determined substantially by the nature of the dyeing unit and of the liquor pick-up resulting therefrom, by the form in which the subsequent addition is made, and of the dyeing temperature. In general, it must be said that only readily soluble products ensure sufficiently dependable results and are thus suitable for the utility of this invention. Whitener solutions make possible a higher loading of fluorescent whitening agent and thus a more rapid exhaustion onto the fibre. Liquid storable commercial formulations of preferably high concentration are also desirable for economic reasons (transportation).

The salts of this invention are preferably employed in the form of aqueous 10–35% solutions. They are obtained by dissolving the free amines in water with addition of the desired acid such as formic acid, acetic acid, propionic acid, glycolic acid, sulfamic acid, phosphorous acid, methanephosphonic acid, ethanephosphonic acid, propanephosphonic acid, butanephosphonic acid, methanesulfonic acid, ethanesulfonic acid, propanesulfonic acid or butanesulfonic acid. The salts, which are isolated as solids, can also be dissolved in water.

The solutions of salts of the stronger acids, such as the solutions of the alkanesulfonates, alkanephosphonates, formates and, in particular, the phosphites and sulfamates, have good long-term heat stability, which is necessary for storage at elevated temperature without precipitation caused by decomposition. No excess, or only a small excess, of acid is necessary for their preparation. The solid salt forms too undergo no decomposition during storage at elevated temperature.

The aqueous solutions of the readily volatile weak acids, in particular of acetic acid, have very good low temperaure resistance, which is necessary for transportation at low temperature. An excess of these solutions is preferably used, as they lower the pH only insignificantly. The preferred pH range is from 2 to 5. Such solutions can be cooled to quite low temperatures without gelling or crystallising. It is not necessary to add solubility stabilisers or hydrotropic agents.

Good resistance to heat and to low temperature is achieved in particular with aqueous solutions of a pyrazoline base with mixtures of different anions. Mixtures of a stronger acid such as sulfamic acid, phosphorous acid, methanephosphonic acid or formic acid with a weak acid, preferably acetic acid, are particularly suitable. The water-solubility is moreover again increased with such mixtures of acids. Thus it is possible to obtain solutions which are stable at room temperature and have an extremely high concentration (up to 70%) of fluorescent whitening agent. Such solutions cannot be obtained with the individual components. The use of mixtures of acids instead of individual acids effects a further lowering of the gelling temperature on cooling. Mixtures of three and more acid components can also be used.

EXAMPLE 1

To a mixture of 24.8 g of the compound of formula

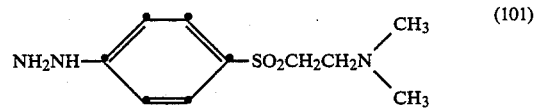

(98.1%) in 30 ml of ethanol and 10 ml of water are added 19.7 g of concentrated hydrochloric acid and the mixture is heated to 75° C. Then a warm solution of 40° C. of 20.9 g of the compound of formula

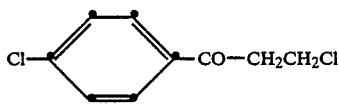 (102)

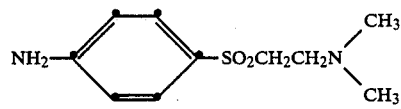 (106)

(97%) in 20 ml of ethanol is added dropwise, with stirring, over half an hour. The batch is stirred overnight at reflux temperature. To the suspension of the resultant pyrazoline hydrochloride are added c. 29 ml of 30% aqueous sodium hydroxide solution at 50°-60° C. until a constant pH of 11-12 is produced and the batch is then cooled. The precipitated product is filtered with suction and washed repeatedly with ethanol and then with water. The filter cake is vacuum dried at 60° C., affording 32.5 g of the compound of formula with a melting point of 135°-136° C. The product can be recrystallised from water, isopropanol or toluene (m.p. 136°-137° C.).

The above two reaction steps can also be carried out consecutively in the same reaction vessel without isolation of the intermediate of formula (105).

With stirring and cooling, 283.5 g of concentrated hydrochloric acid are added to a suspension of 182.6 g of the compound of formula (106) in 500 ml of water. A solution of 56 g of sodium nitrite in 100 ml of water is

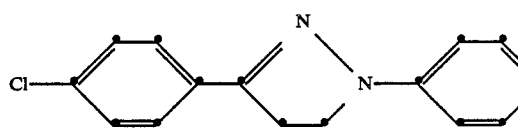 (103)

with a melting point of 157°-158° C.

The starting compound of formula (101) can be prepared as follows: With stirring and cooling, 30% sodium hydroxide solution is added dropwise at room temperaure to a suspension of 586.6 g of the compound of formula

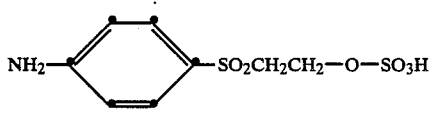 (104)

(95.9%) in 2 liters of water until a constant pH of 10-11 is produced (consumption: 420 ml). The starting material gradually dissolves during this addition and the reaction product then precipitates. The thick suspension is stirred for half an hour at room temperature and filtered with suction. The residue is washed with water until free of salt, affording 418.6 g of moist product, corresponding to 336.2 g of dry product of the compound of formula

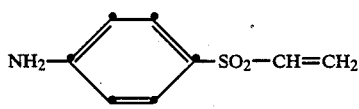 (105)

Melting point: 71°-72° C.

The 418.6 g of the still moist product are stirred in 500 ml of water. To the resultant suspension are added 271 g of an aqueous 40% aqueous solution of dimethylamine, whereupon the temperature rises slightly. The starting material dissolves during this addition and the reaction product precipitates. The suspension is slowly heated to 85° C., kept for 1 hour at 85° C., cooled, and filtered with suction. The residue is washed with 300 ml of ice-water and vacuum dried at 80° C., affording 402.0 g of the compound of formula added dropwise over ½ hour at 0°-5° C. to the above solution. The mixture is stirred for 1 hour at the same temperature, if necessary correcting with sulfamic acid or sodium nitrite (test with potassium iodide starch indicator), and the solution of the diazonium salt is added dropwise, with stirring and further cooling, over c. 50 minutes to 624.3 g of an aqueous 40% solution of sodium bisulfite which has been adjusted beforehand to pH 6-7 with 30% sodium hydroxide solution (105 ml). The pH is kept at 7 by the simultaneous dropwise addition of further sodium hydroxide solution. Total consumption of sodium hydroxide solution: 183 ml. The solution is heated to 60° C. and 243 g of concentrated hydrochloric acid are added cautiously, so that the evolution of sulfur dioxide gas can be kept under control. After stirring for 4 hours at 90° C., the solution is cooled to 0°-5° C. and adjusted with 30% sodium hydroxide solution (c. 400 ml) to pH 10-12, whereupon the hydrazine precipitates in the form of the free base. It is sensitive to strong alkalies (violet colouration). After filtration by suction, the residue is purified by stirring it in 2 liters of methylene chloride, removing insoluble salt by filtration, separating the upper aqueous phase in a separating funnel and drying the methylene chloride phase. (It is advantageous to extract the hydrazine twice with methylene chloride from the alkaline aqueous phase). The methylene chloride is removed by evaporation, the residue is crystallised from 500 ml of isopropanol, filtered at 5° C. and washed with 2×50 ml of ice-cooled isopropanol, affording 160.8 g of the compound of formula (101) with a melting point of 126°-128° C.

Instead of using methylene chloride, it is also possible to perform the extraction with ethanol and to react the resultant ethanolic solution, as described at the outset, direct with the compound of formula (102).

Instead of isolating the hydrazine of formula (101), the acid reaction solution obtained in the synthesis, which contains the hydrazine (101) as salt (dihydrochloride of m.p. ~135° C. (dec.) and dihydrosulfate) can also be reacted direct with the compound of formula (102) after addition of alkali until the pH is 2-3. The initially precipitated pyrazoline salt (mainly the hydrochloride of the base of formula (103), m.p. 249°-250° C.) is conveniently isolated by filtraton and purified by repeatedly washing with ethanol. After the reaction with sodium hydroxide solution in ethanol, as described at the outset, the pyrazoline of formula (103) is obtained in high purity.

EXAMPLE 2

To an acid solution of the hydrazine of formula (101), obtained from 117.3 g of the compound of formula (106) (97.3%), are added 50 ml of acetone at room temperature. With stirring, 30% sodium hydroxide solution (220 ml) is added dropwise to the solution until a constant pH of 11 is obtained. The precipitated product is filtered with suction, washed free of salt with water, and dried, affording 125.5 g of the compound of formula

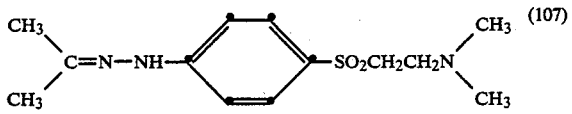

with a melting point of 121°–122° C. (after recrystallization from isopropanol or toluene).

28.4 g of the acetone hydrazone of formula (107) are dissolved in 30 ml of water and 17.0 ml of concentrated hydrochloric acid and the solution is heated to the boil with stirring. A mixture of 7.1 ml of acetone and water is distilled off over 2 hours. Then a solution of 20.8 g of the compound of formula (102) (98%) in 20 ml of ethanol is added dropwise at 85° C. over ½ hour and the procedure is continued as described in Example 1. Yield: 29.3 g of the compound of formula (103).

EXAMPLE 3

10.4 g of 1-(p-vinylsulfonylphenyl)-3-(p-chlorophenyl)-2-pyrazoline are stirred in 7.2 ml of 2-methylaminoethanol at 130° C. After 3 hours, the solution is allowed to cool and diluted while still hot with 50 ml of isopropanol. The precipitate is isolated by suction filtration, washed with isopropanol and dried, affording 10.8 g of the compound of formula

with a melting point of 131°–132° C. (after recrystallisation from perchloroethylene and isopropanol).

1-[p-(Dihydroxyethyl)aminoethylsulfonylphenyl]-3-(p-chlorophenyl)-2-pyrazoline of m.p. 126°–128° C. (after recrystallisation from toluene and isopropanol) is obtained in analogous manner.

The compound of formula (108) can be prepared in accordance with Example 1. The corresponding hydrazine of formula

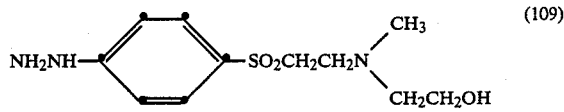

is a highly viscous liquid which slowly congeals on storage. Acetone hydrazone of m.p. 114°–115° C.

EXAMPLE 4

6.9 g of 1-(p-vinylsulfonylphenyl)-3-(p-chlorophenyl)-2-pyrazoline are stirred in 5.5 g of a 33% solution of dimethylamine in ethanol and 15 ml of ethanol. The solution is heated gradually over one hour to 78° C. and stirring is continued until the starting material is dissolved and a concentrated sample is soluble in dilute acetic acid. The solution is allowed to cool to room temperature, whereupon a dense precipitate of the reaction product forms. This precipitate is collected by suction filtration, washed with ethanol and dried, affording 6.7 g of 1-(p-dimethylaminoethylsulfonylphenyl)-3-(p-chlorophenyl)-2-pyrazoline (formula 103).

1-(p-Diethylaminoethylsulfonylphenyl)-3-(p-chlorophenyl)-2-pyrazoline (m.p. 104°–107° C.) is obtained in analogous manner using diethylamine in isopropanol instead of dimethylamine in ethanol.

EXAMPLE 5

7.8 g of the compound of formula (103) and 1.7 g of phosphorous acid are stirred in 50 ml of ethanol for 10 minutes at reflux temperature. The thick suspension is allowed to cool to room temperature, filtered with suction, and the residue is washed repeatedly with ethanol and dried at 90° C. under a high vacuum, affording 9.1 g of the compound of formula

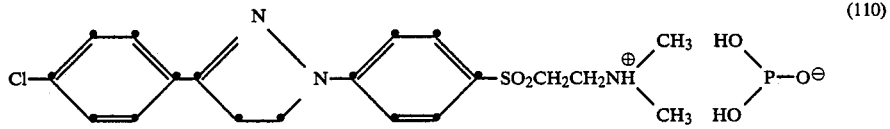

with a melting point of 154° C.

EXAMPLE 6

7.85 g of the compound of formula (103) and 1.95 g of sulfamic acid are stirred in 25 ml of water at room temperaure. The resultant solution is concentrated by evaporation almost completely at room temperaure under a high vacuum and the residue is stirred in c. 50 ml of methanol. The crystalline product is collected by suction filtration, washed repeatedly with water and dried over calcium chloride at room temperature under a high vacuum, to give the compound of formula

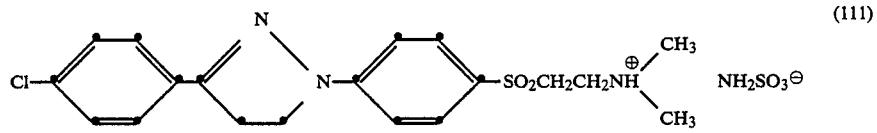

(111)

as an almost colourless product (m.p. c. 136° C., unsharp).

EXAMPLE 7

7.8 g of the compound of formula (103) and 2.1 g of methanephosphonic acid are boiled in 100 ml of isopropanol. The mixture is cooled to room temperature, the precipitate is isolated by suction filtration, washed twice with isopropanol and dried under a high vacuum at room temperature, affording 9.6 g of the compound of formula

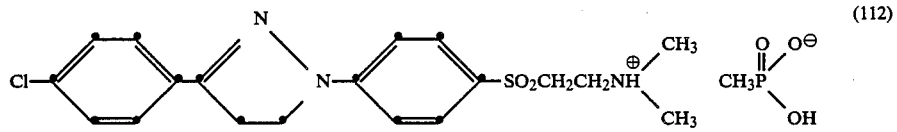

(112)

in the form of almost colourless water-soluble crystals of m.p. 146° C. The solubility of this product in water at room temperature is over 40%.

EXAMPLE 8

165.0 g of the base of formula (103) and 34.5 g of phosphorous acid are stirred in 500 ml of water at room temperature. To the resultant solution are added 110 g of glacial acetic acid and the mixture is diluted with water to a total weight of 1100 g. A slight turbidity caused by the presence of impurities may be removed by a clarifying filtration. The resultant 15% solution (based on the starting material) has a pH of 2.7 at a gelatin temperature of below 0° C. and has good heat stability on storage at 60° C.

A product with similar properties is obtained by using 40.9 g of sulfamic acid in this Example instead of phosphorous acid.

EXAMPLE 9

4 different batches are prepared by stirring 50.0 g of the compound of formula (103) into
(a) 20.0 g of 85% formic acid
 20.0 g of acetic acid
(b) 12.9 g of methanephosphonic acid
 20.0 g of acetic acid
(c) 12.3 g of methanesulfonic acid
 20.0 g of acetic acid
(d) 27.5 g of glycolic acid
 20.0 g of acetic acid
and sufficient water to give a total weight of 166.6 g. The 30% solutions so obtained (based on starting material) have a pH of 2.4 to 3.0.

EXAMPLE 10

In accordance with Example 8, 15% aqueous solutions of compounds of formula

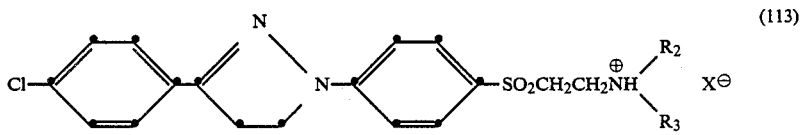

(113)

(a) $R_2=CH_3$, $R_3=-CH_2CH_2OH$
(b) $R_2=R_3=-CH_2CH_2OH$
(c) $R_2=R_3=-CH_2CH_3$ are obtained, wherein X is the phosphite ion and the acetate ion.

EXAMPLE 11

Concentrated hydrochloric acid (c. 6 ml) is added dropwise to a suspension of 12.1 g of benzal 4-chloroacetophenone and 12.7 g of the compound of formula (101) in 150 ml of n-propanol until the pH is 2.5. The mixture is heated for 20 hours at reflux temperature and the pH is kept at 2.5 by occasional dropwise addition of 30% aqueous sodium hydroxide solution. When the reaction is complete, the batch is cooled to 60° C. and, with efficient stirring, further sodium hydroxide solution is added until a permanent pH of c. 13 is attained. After cooling, the precipitated product is isolated by suction filtration and washed repeatedly with n-propanol and then with water until free of chloride, to give 20.1 g of the compound of formula

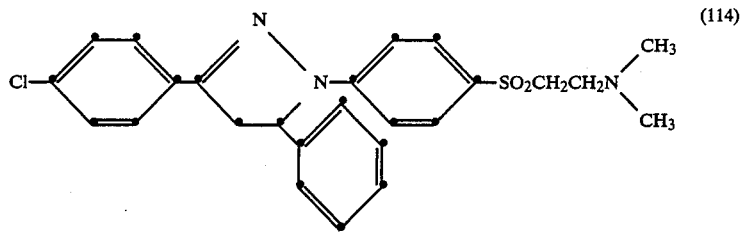

of m.p. 166°–167° C. (after recrystallization from nonane and n-propanol).

EXAMPLE 12

The use of 3,3′,4′-trichloro-6′-methylpropiophenone instead of the compound of formula (102) in Example 1 gives the compound of formula

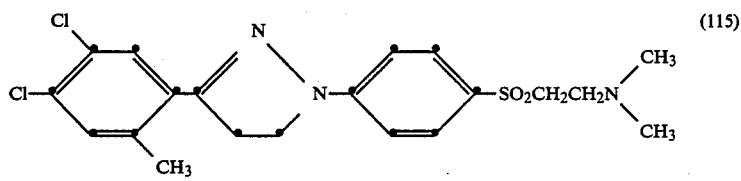

Melting point: 163° C. (recrystallisation from n-propanol).

EXAMPLE 13

With stirring, 1.14 ml of dimethyl sulfate are added dropwise at reflux temperature to a solution of 3.9 g of 1-(p-dimethylaminoethylsulfonylphenyl)-3-(p-chlorophenyl)-2-pyrazoline in 50 ml of methyl ethyl ketone. After 1 hour the mixture is cooled, the precipitated product is isolated by suction filtration and washed repeatedly with methyl ethyl ketone and dried, affording 4.7 g of the compound of formula

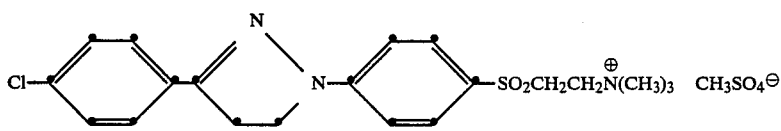

with a melting point of 211° C.

In analogous manner, the compound of formula

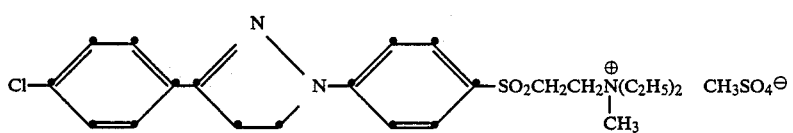

(m.p. 173° C.) is obtained from 1-(p-diethylaminoethylsulfonylphenyl)-3-(p-chlorophenyl)-2-pyrazoline.

EXAMPLE 14

An acrylic fabric (Orlon 75) is treated on a dyeing machine at a liquor to goods ratio of 1:20 with an aqueous bath containing 0.1% of a fluorescent whitening agent of formula (108), (110), (111), (112), (113 a–c), (115) or (116), based on the weight of the goods, 1 g/l of an adduct of 35 moles of ethylene oxide and 1 mole of stearyl alcohol, and 1 ml/l of acetic acid. The application is made in accordance with the following temperature program: 40°–97° C./30 minutes, 97° C./30 minutes, 97°–40° C./15 minutes. The acrylic fabric is then rinsed for 30 seconds in running, softened water and dried at 70° C. in a drying cabinet. An excellent white effect is obtained on the treated fabric.

Similar effects are obtained by using modified acrylic fabric (Courtelle fabric).

EXAMPLE 15

A cellulose acetate fabric is put at 50° C. and at a liquor to goods ratio of 1:40 into an aqueous bath containing 0.15%, based on the weight of goods, of a compound of formula (108) or (110–113). The temperaure of the treatment bath is raised to 90°–95° C. and kept in this range for 30 to 45 minutes. The goods are then rinsed and dried. A strong white effect is obtained on the treated fabric.

EXAMPLE 16

Polyamide 6,6 woven tricot fabric is treated at a liquor to goods ratio of 1:20 with an aqueous bath which contains 0.2%, based on the weight of the fabric, of a compound of formula (108) or (110–113), and 1 g/l of an alkylphenol polyglycol ether. The bath is heated to 130° C. over 30 minutes, kept for 30 minutes at this temperature, and then cooled to 40° C. over 15 minutes. The fabric is subsequently rinsed in running deionised water and dried at 180° C. with an iron. A good white effect is obtained on the treated polyamide fabric in all cases.

EXAMPLE 17

Freshly spun acrylic wet cable (3.0 g dry weight) is immersed while still moist at 45° C. for 4 seconds in 100 ml of an aqueous liquor which contains 0.0005% of a fluorescent whitening agent of formula (110) to (113) and has been adjusted to pH 4 with a concentrated solution of acetic acid. The wet cable is subsequently rinsed briefly with water and dried at 90°–100° C. A good white effect is obtained on the acrylic fabric.

Stronger white effects are obtained by increasing the concentration of fluorescent whitening agent to e.g. 0.005%.

EXAMPLE 18

Rinsed and stretched, non-dried acrylic cable obtained by the sodium thiocyanate wet spinning process is immersed at a liquor to goods ratio of 1:100 at 45° C. for 4 seconds in an aqueous solution which contains 0.1 g/l of a fluorescent whitening agent described in Example 8 or 9 and 0.5 ml of 85% formic acid (pH of the solution: 4).

The goods are then rinsed briefly in water and dried at 95° C. in the air. A strong white effect is obtained on the treated acrylic cable.

What is claimed is:

1. A pyrazoline compound selected from the group consisting of

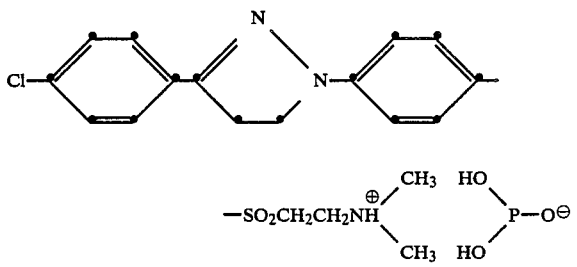

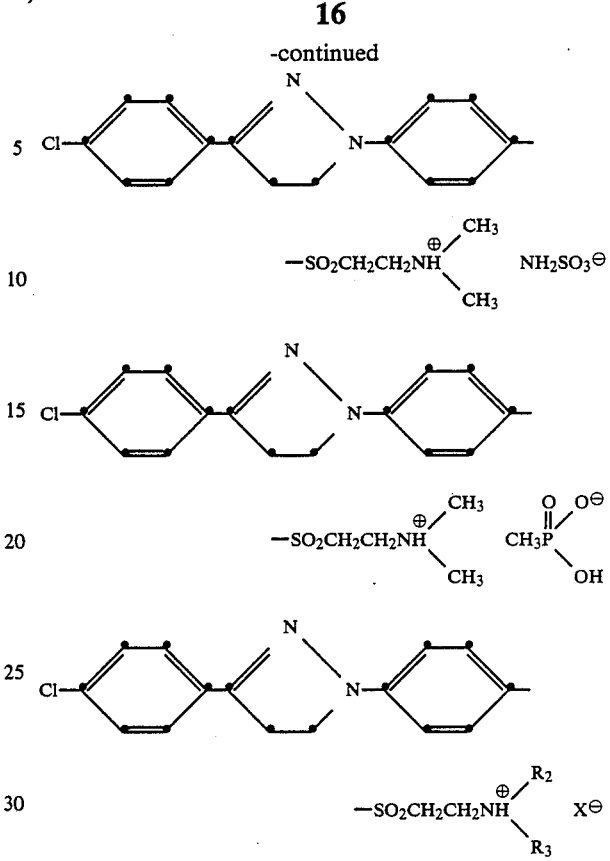

wherein X is the phosphite ion and
(a) $R_2=CH_3$, $R_3=-CH_2CH_2OH$
(b) $R_2=R_3=-CH_2CH_2OH$
(c) $R_2=R_3=-CH_2CH_3$.

2. A process for whitening acrylic, cellulose acetate or polyamide fibres, which comprises treating said fibres with a pyrazoline compound as claimed in claim 1 or with a mixture of said compounds.

3. A process according to claim 2 for whitening acrylic fibres in the gel state.

* * * * *